(12) United States Patent
Stulen et al.

(10) Patent No.: US 9,017,849 B2
(45) Date of Patent: Apr. 28, 2015

(54) POWER SOURCE MANAGEMENT FOR MEDICAL DEVICE

(75) Inventors: Foster B. Stulen, Mason, OH (US); Richard W. Timm, Cincinnati, OH (US); William D. Dannaher, Cincinnati, OH (US); Danius P. Silkaitis, Mason, OH (US); Michael J. Stokes, Cincinnati, OH (US); Jeffrey L. Aldridge, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/276,745

(22) Filed: Oct. 19, 2011

(65) Prior Publication Data

US 2012/0115005 A1 May 10, 2012

Related U.S. Application Data

(60) Provisional application No. 61/410,603, filed on Nov. 5, 2010, provisional application No. 61/487,846, filed on May 19, 2011.

(51) Int. Cl.
*H01M 10/50* (2006.01)
*A61B 17/00* (2006.01)
(Continued)

(52) U.S. Cl.
CPC ....... *A61B 18/1442* (2013.01); *A61B 17/00234* (2013.01); *A61B 17/285* (2013.01); *A61B 17/320068* (2013.01); *A61B 2017/2933* (2013.01); *A61B 17/320092* (2013.01); *A61B 18/00* (2013.01); *A61B 18/1445* (2013.01); *A61B 18/14* (2013.01); *A61B 2017/2931* (2013.01); *A61B 2017/294* (2013.01); *A61B 2019/4815* (2013.01); *A61B 2017/00734* (2013.01); *A61B 2019/4873* (2013.01); *A61B 2018/1226* (2013.01); *A61B 2017/291* (2013.01); *A61B 18/04* (2013.01); *H02J 7/0045* (2013.01); *A61B 2017/293* (2013.01); *A61B 2017/2929* (2013.01); *A61B 2018/1455* (2013.01); *A61B 2017/00473* (2013.01); *A61B 2018/1412* (2013.01); *A61B 19/38* (2013.01); *A61B 2017/00084* (2013.01);
(Continued)

(58) Field of Classification Search
None
See application file for complete search history.

(56) References Cited

U.S. PATENT DOCUMENTS 1,754,806 A 4/1930 Stevenson
3,297,192 A 1/1967 Swett
(Continued)

FOREIGN PATENT DOCUMENTS

DE 102008051866 10/2010
DE 102009013034 10/2010
(Continued)

OTHER PUBLICATIONS

U.S. Appl. No. 13/151,471, filed Jun. 2, 2011, Stulen.
(Continued)

*Primary Examiner* — Ula C Ruddock
*Assistant Examiner* — Matthew Van Oudenaren (57) ABSTRACT

A surgical instrument includes a handle assembly, a battery pack, and a cooling device. The battery pack is operable to power the surgical instrument and may be inserted into the handle assembly. The cooling device is mechanically integrated with the battery pack. The cooling device is further operable to draw heat away from the battery pack while the battery pack delivers power to the surgical instrument.

14 Claims, 8 Drawing Sheets

(51) Int. Cl.
   *A61B 17/32* (2006.01)
   *A61B 18/00* (2006.01)
   *A61B 18/14* (2006.01)
   *A61B 18/04* (2006.01)
   *H02J 7/00* (2006.01)
   *A61B 17/285* (2006.01)
   *A61B 17/29* (2006.01)
   *A61B 19/00* (2006.01)
   *A61B 18/12* (2006.01)
   *A61B 17/064* (2006.01)

(52) U.S. Cl.
   CPC ............... *A61B 2019/4868* (2013.01); *A61B 2018/00178* (2013.01); *A61B 18/1233* (2013.01); *A61B 18/12* (2013.01); *A61B 17/064* (2013.01); *A61B 2017/00398* (2013.01); *A61B 2017/00477* (2013.01); *A61B 2018/00791* (2013.01); *A61B 2017/00482* (2013.01); *A61B 2018/00988* (2013.01); *A61B 2017/0046* (2013.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A * | 12/1992 | Savovic et al. ............ 429/157 |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekumas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekumas |
| 5,630,456 A | 5/1997 | Hugo et al. |
| 5,690,222 A | 11/1997 | Peters |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,099,537 A | 8/2000 | Sugai et al. |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,325,811 B1 | 12/2001 | Messerly |
| 6,339,368 B1 * | 1/2002 | Leith ..................... 340/384.4 |
| 6,398,755 B1 | 6/2002 | Belef et al. |
| 6,409,742 B1 | 6/2002 | Fulton, III et al. |
| 6,475,680 B1 * | 11/2002 | Arai et al. ................ 429/340 |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,609,414 B2 | 8/2003 | Mayer et al. |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 | 4/2004 | Olewine et al. |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,783,524 B2 | 8/2004 | Anderson et al. |
| 6,815,206 B2 | 11/2004 | Lin et al. |
| 6,821,671 B2 * | 11/2004 | Hinton et al. .............. 429/120 |
| 6,838,862 B2 | 1/2005 | Luu |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |

(56) References Cited

U.S. PATENT DOCUMENTS

| | | |
|---|---|---|
| 7,563,142 B1 | 7/2009 | Wenger et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,550,106 B2 | 10/2013 | Hebach et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2004/0253130 A1* | 12/2004 | Sauciuc et al. ................. 417/436 |
| 2005/0021065 A1 | 1/2005 | Yamada et al. |
| 2005/0033195 A1 | 2/2005 | Fulton, III et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1* | 9/2007 | Curello et al. ................. 429/25 |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2007/0297137 A1* | 12/2007 | Glahn et al. ................. 361/699 |
| 2008/0003491 A1* | 1/2008 | Yahnker et al. ................. 429/62 |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1* | 7/2008 | Ping ............................. 220/581 |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1* | 6/2009 | Palmer et al. ................. 606/169 |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko et al. |
| 2011/0077514 A1 | 3/2011 | Ulric et al. |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2012/0179036 A1 | 7/2012 | Patrick et al. |
| 2012/0265230 A1 | 10/2012 | Yates et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |

(56) References Cited

U.S. PATENT DOCUMENTS

| | | | |
|---|---|---|---|
| 2013/0090552 A1 | 4/2013 | Ramamurthy et al. | |
| 2013/0116690 A1 | 5/2013 | Unger et al. | |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., "Partially Implantable Vibrating Ossicular Prosthesis, Transducers'97, vol. 1, International Conference on Solid State Sensors and Actuators, (Jun. 16-19, 1997) pp. 433-436 (Abstract). System 6 Aseptic Battery System," Stryker (2006) pp. 1-2.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
International Search Report dated Jan. 12, 2012 for Application No. PCT/US2011/059226.
International Search Report dated Jan. 26, 2012 for Application No. PCT/US2011/059220.
International Search Report dated Feb. 1, 2012 for Application No. PCT/US2011/059223.
International Search Report dated May 29, 2012 for Application No. PCT/US2011/059358.
International Search Report and Written Opinion dated Jul. 6, 2012 for Application No. PCT/US2011/059381.
Restriction Requirement dated Dec. 11, 2012 for U.S. Appl. No. 13/151,481.

(56) References Cited

OTHER PUBLICATIONS

Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Feb. 28, 2013 for U.S. Appl. No. 13/270,667.
Office Action Non Final dated Apr. 26, 2013 for U.S. Appl. No. 13/270,667.
Office Action Non-Final dated Jun. 14, 2013 for U.S. Appl. No. 13/151,498.
Restriction Requirement dated Feb. 6, 2013 for U.S. Appl. No. 13/276,687.
Office Action Non-Final dated Jun. 12, 2013 for U.S. Appl. No. 13/276,687.
Restriction Requirement dated Apr. 29, 2013 for U.S. Appl. No. 13/274,830.
Office Action Non-Final dated Jun. 14, 2013 for U.S. Appl. No. 13/274,830.
Restriction Requirement dated Mar. 13, 2013 for U.S. Appl. No. 13/151,509.
Restriction Requirement dated Jun. 24, 2013 for U.S. Appl. No. 13/151,509.
Restriction Requirement dated Jul. 5, 2013 for U.S. Appl. No. 13/151,488.
Office Action Non-Final dated Aug. 6, 2013 for U.S. Appl. No. 13/151,471.
Office Action Non-Final dated Dec. 21, 2012 for U.S. Appl. No. 13/274,516.
Office Action Final dated Aug. 16, 2013 for U.S. Appl. No. 13/274,516.
Office Action Non-Final dated Dec. 21, 2012 for U.S. Appl. No. 13/276,673.
Office Action Non-Final dated Aug. 19, 2013 for U.S. Appl. No. 13/276,673.
Office Action Non-Final dated Feb. 1, 2013 for U.S. Appl. No. 13/275,563.
Office Action Final dated Aug. 29, 2013 for U.S. Appl. No. 13/275,563.
Office Action Non-Final dated Apr. 1, 2013 for U.S. Appl. No. 13/274,805.
Office Action Final dated Sep. 12, 2013 for U.S. Appl. No. 13/274,805.
Restriction Requirement dated Feb. 25, 2013 for U.S. Appl. No. 13/274,540.
Office Action Non-Final dated Apr. 30, 2013 for U.S. Appl. No. 13/274,540.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Restriction Requirement dated Feb. 6, 2013 for U.S. Appl. No. 13/276,660.
Office Action Non-Final dated Jun. 3, 2013 for U.S. Appl. No. 13/246,660.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
European Communication dated Feb. 19, 2014 for Application No. EP 11781972.2.
International Preliminary Report on Patentability for Application No. PCT/US2011/059212 dated May 7, 2013.
International Preliminary Report on Patentability for Application No. PCT/US2011/059215 dated May 8, 2013.
International Preliminary Report on Patentability for Application No. PCT/US2011/059217 dated May 7, 2013.
International Preliminary Report on Patentability for Application No. PCT/US2011/059218 dated May 7, 2013.
International Preliminary Report on Patentability for Application No. PCT/US2011/059220 dated May 7, 2013.
International Preliminary Report on Patentability for Application No. PCT/US2011/059222 dated May 7, 2013.
International Preliminary Report on Patentability for Application No. PCT/US2011/059223 dated May 7, 2013.
International Preliminary Report on Patentability for Application No. PCT/US2011/059226 dated May 7, 2013.
International Preliminary Report on Patentability for Application No. PCT/US2011/059338 dated May 7, 2013.
International Preliminary Report on Patentability for Application No. PCT/US2011/059315 dated May 7, 2013.
International Preliminary Report on Patentability for Application No. PCT/US2011/059354 dated May 7, 2013.
International Preliminary Report on Patentability for Application No. PCT/US2011/059358 dated May 7, 2013.
International Preliminary Report on Patentability for Application No. PCT/US2011/059362 dated May 7, 2013.
International Preliminary Report on Patentability for Application No. PCT/US2011/059365 dated May 8, 2013.
International Preliminary Report on Patentability for Application No. PCT/US2011/059371 dated May 7, 2013.
International Preliminary Report on Patentability for Application No. PCT/US2011/059378 dated May 7, 2013.
International Preliminary Report on Patentability for Application No. PCT/US2011/059381 dated May 7, 2013.
Notice of Allowance dated Dec. 6, 2013 for U.S. Appl. No. 13/151,471.
Office Action Non-Final dated Mar. 28, 2014 for U.S. Appl. No. 13/151,471.
Office Action Final dated Nov. 21, 2013 for U.S. Appl. No. 13/151,498.
Office Action Non Final dated Mar. 18, 2014 for U.S. Appl. No. 13/151,498.
Office Action Non Final dated Jun. 18, 2014 for U.S. Appl. No. 13/151,503.
Office Action Non-Final dated Sep. 26, 2013 for U.S. Appl. No. 13/151,509.
Office Action Final dated Jan. 29, 2014 for U.S. Appl. No. 13/151,509.
Restriction Requirement dated Jun. 11, 2014 for U.S. Appl. No. 13/151,512.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Non-Final dated Dec. 16, 2013 for U.S. Appl. No. 13/274,516.
Office Action Final dated Jun. 12, 2014 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Office Action Non-Final dated Jan. 6, 2014 for U.S. Appl. No. 13/275,514.

(56) References Cited

OTHER PUBLICATIONS

Office Action Final dated Feb. 28, 2014 for U.S. Appl. No. 13/275,547.
Office Action Final dated Mar. 21, 2014 for U.S. Appl. No. 13/276,673.
Notice of Allowance dated Nov. 12, 2013 for U.S. Appl. No. 13/276,687.
Notice of Allowance dated Jun. 2, 2014 for U.S. Appl. No. 13/276,687.
Office Action Final dated Sep. 27, 2013 for U.S. Appl. No. 13/276,707.
Office Action Non-Final dated Aug. 20, 2014 for U.S. Appl. No. 13/276,725.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,481.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Restriction Requirement, dated Sep. 24, 2014 for U.S. Appl. No. 13/277,328.

* cited by examiner

POWER SOURCE MANAGEMENT FOR MEDICAL DEVICE

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

Many medical devices require a power source to function properly. In some cases, medical devices may be plugged into a wall outlet to receive power. However, tethering a medical device to a wall outlet may be cumbersome or difficult to maneuver for the user. In other scenarios, medical devices may be connected to an intermediate power supply or other piece of capital equipment located between the medical device and a wall outlet. Using such an intermediate power source may also be cumbersome and difficult. Furthermore, in many situations, such medical devices must remain sterile; otherwise a patient may be susceptible to infection or other contamination from being exposed to a non-sterile device. Battery packs could be used with such medical devices. However, such battery packs may be non-sterile. Thus, using a battery could pose increased risks to a patient. In the event that a non-sterile battery is used, the sterile medical device may ultimately become exposed to the battery, which may compromise the sterility of the medical device for use with a patient. In short, using a non-sterile power source with a sterile medical device may pose a variety of risks. As a battery or battery pack delivers power, the battery may also generate heat within the battery. If being used in a surgical instrument in a surgical setting, such heat may be dangerous or otherwise pose risks. In other exemplary situations, heat may simply cause discomfort or may be otherwise undesirable.

Merely exemplary surgical devices that rely on electrical power are disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pat. Pub. No. 2009/0143797, entitled "Cordless Hand-held Ultrasonic Cautery Cutting Device," published Jun. 4, 2009 and issued on Apr. 16, 2013 as U.S. Pat. No. 8,419,757, the disclosure of which is incorporated by reference herein; U.S. Pub. No. 2009/0209990 entitled "Motorized Surgical Cutting and Fastening Instrument Having Handle Based Power Source," published Aug. 20, 2009, the disclosure of which is incorporated by reference herein; U.S. Pub. No. 2010/0069940 entitled "Ultrasonic Device for Fingertip Control," published Mar. 18, 2010, the disclosure of which is incorporated by reference herein; and U.S. Pub. No. 2011/0015660, entitled "Rotating Transducer Mount for Ultrasonic Surgical Instruments," published Jan. 20, 2011 and issued on Jun. 11, 2013 as U.S. Pat. No. 8,461,744, the disclosure of which is incorporated by reference herein. It should be understood that the devices described in the above-cited references may be readily adapted to include an integral power source, such as those described herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Additional exemplary devices that may be adapted to include a portable power source are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, the disclosure of which is incorporated by reference herein; and U.S. patent application Ser. No. 13/151,481 and published on May 10, 2012 as U.S. Pub. No. 2012/011637913/151,181, entitled "Motor Driven Electrosurgical Device with Mechanical and Electrical Feedback," filed Jun. 2, 2011, the disclosure of which is incorporated by reference herein. The devices described in those references may also be readily adapted to include an integral power source, such as those described herein.

While several systems and methods have been made for use with an electrically powered medical device, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Medical Devices for Use with Insertable or Reclaimable Components

Figure 1:
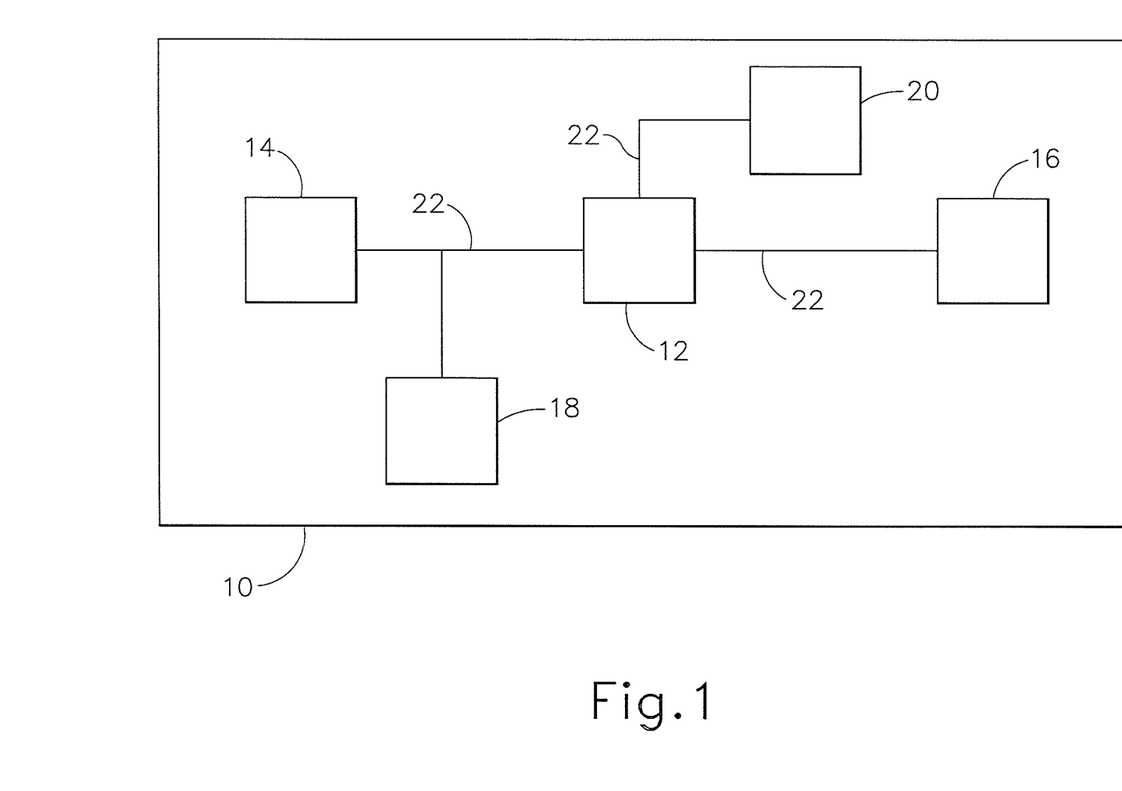
FIG. 1 depicts a schematic view of an exemplary medical device having an internal power source.

FIG. 1 shows components of an exemplary medical device and/or surgical instrument (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
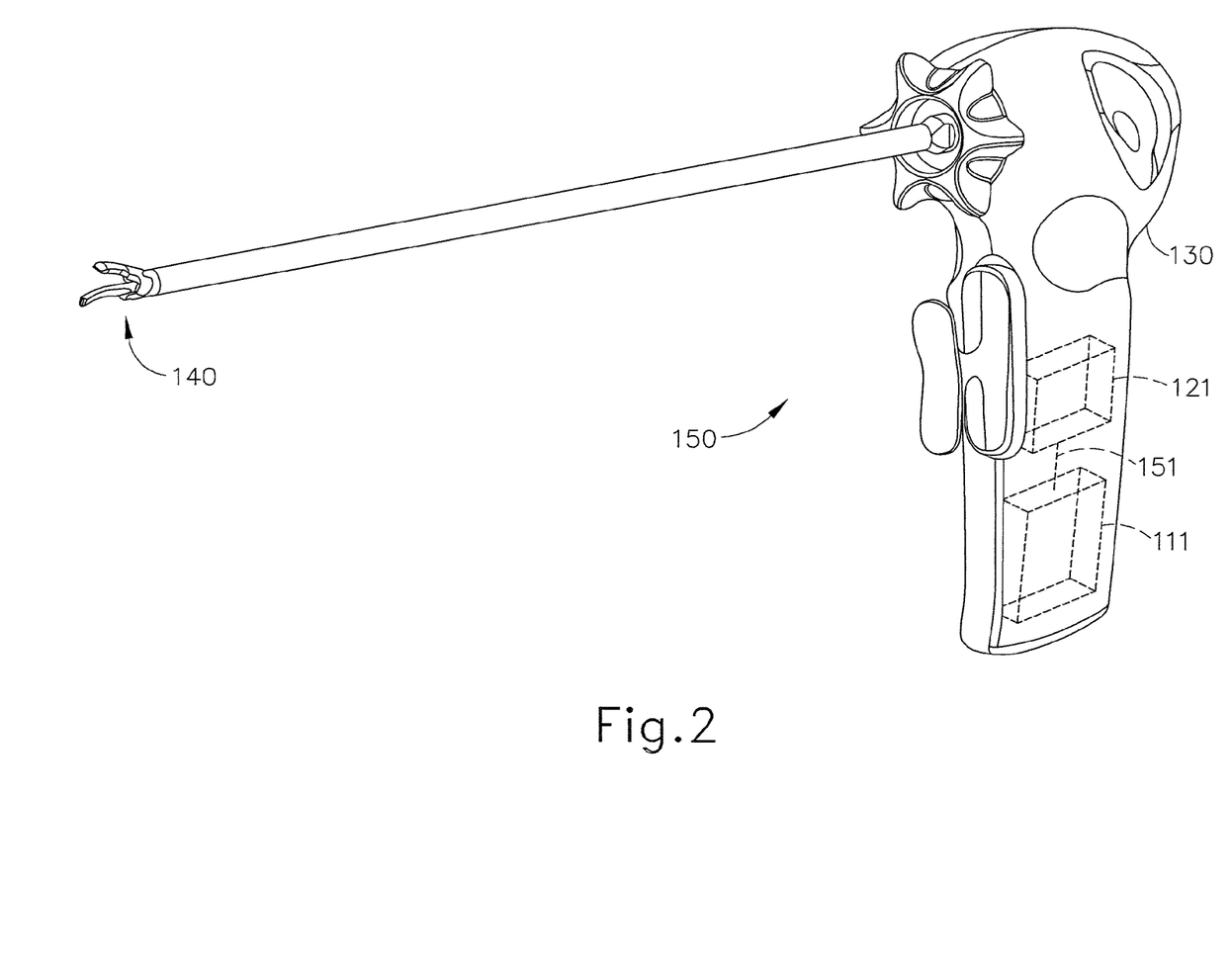
FIG. 2 depicts a perspective view of an exemplary medical device having an internal power source.

FIG. 2 depicts a merely exemplary form that medical device (10) may take. In particular, FIG. 2 shows a medical device (150) comprising a power source (111), a control module (121), a housing (130), end effector (140), and an electrical connection (151). In the present example, power source (111) is located internally within housing (130) of medical device (150). Alternatively, power source (111) may only partially extend into housing (130) and may be selectively attachable to a portion of housing (130). In yet a further exemplary configuration, a portion of housing (130) may extend into power source (111) and power source (111) may be selectively attachable to the portion of housing (130). Power source (111) may also be configured to detach from medical device (150) and decouple from control module (121) or electrical connection (151). As a result, power source (111) may be completely separated from medical device (150) in some versions. As is readily apparent, this may allow the power source (111) to be removed to be recharged or reclaimed for resterilization and reuse, such as in accordance with various teachings herein. After recharging, or after an initial charge, power source (111) may be inserted or reinserted into medical device (150) and secured to housing (130) or internally within housing (130). Of course, medical device (150) may also allow power source (111) to be charged and/or recharged while power source (111) is still in or otherwise coupled relative to housing (130).

It should also be understood that control module (121) may be removed for servicing, testing, replacement, or any other purpose as will be apparent to one of ordinary skill in the art in view of the teachings herein. Further, end effector (140) may also be removable from medical device (150) for servicing, testing, replacement, or any other purpose as will be apparent to one of ordinary skill in the art in view of the teachings herein. While certain configurations of an exemplary medical device (150) have been described, various other ways in which medical device (150) may be configured will be apparent to those of ordinary skill in the art in view of the teachings herein. By way of example only, medical devices (10, 150) and/or any other medical device referred to herein may be constructed in accordance with at least some of the teachings of U.S. Pat. No. 6,500,176; U.S. Pat. No. 6,783,524; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pat. No. 7,416,101; U.S. Pat. No. 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0143797; U.S. Pub. No. 2009/0209990; U.S. Pub. No. 2010/0069940; U.S. Pub. No. 2011/0015660; U.S. Pat. Pub. No. 2011/0087218; U.S. patent application Ser. No. 13/151,481 and published on May 10, 2012 as U.S. Pub. No. 2012/0116379; and/or U.S. Provisional Application Ser. No. 61/410,603. The disclosures of each of those documents are incorporated by reference herein in their entirety.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Heat Sinks

Figure 3:
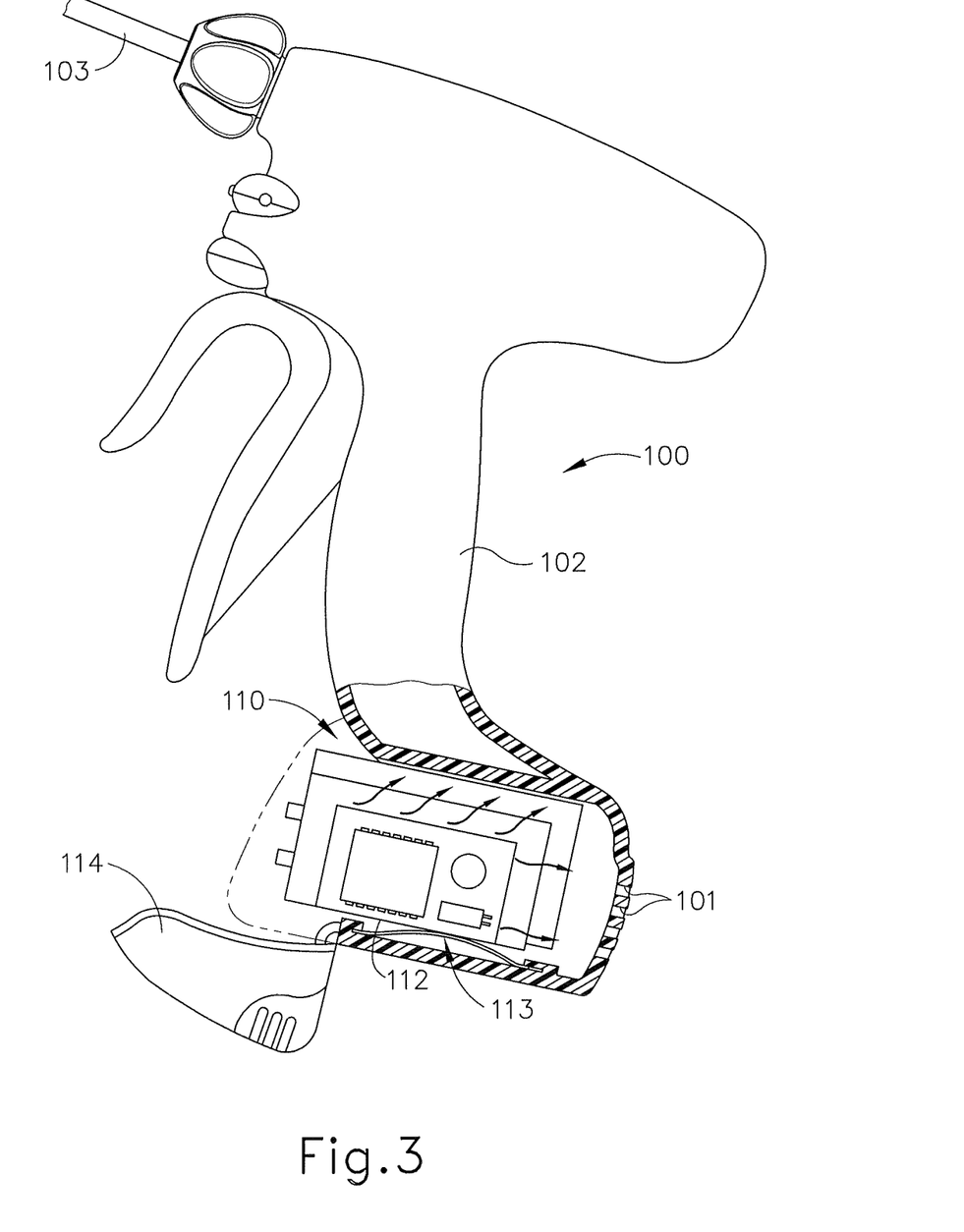
FIG. 3 depicts a side cross sectional view of an exemplary surgical instrument with a battery pack.

It will be appreciated that medical device/surgical instrument (10, 120) may be powered using power source (14, 121), and during the operation of surgical instrument (10, 120), power source (14, 121) may generate heat. It may be desirable in some instances to draw away, remove, dissipate, or otherwise deal with such heat. For example, FIG. 3 shows an exemplary surgical instrument (100) operable to utilize electrical energy to power surgical instrument (100). Surgical instrument (100) comprises a handle assembly (102). A shaft (103) extends distally from handle assembly (102). The distal end of shaft (103) comprises an end effector activated by surgical instrument (100). In the present example, surgical instrument (100) is electrically powered through use of a battery pack (110) contained in a battery compartment (112) of handle assembly (102). A hatch (114) may be opened to facilitate removal and/or insertion of battery pack (110). Hatch (114) comprises a hinged door in the present example, but any suitable opening mechanism may be used as would be apparent to one of ordinary skill in the art in view of the teachings herein.

The user may insert battery pack (110) into handle assembly (102) prior to using surgical instrument (100). Once the user is done using surgical instrument (100), the user may either leave battery pack (110) within handle assembly (102) or may remove battery pack (110) from handle assembly (102). Handle assembly (102) also comprises a leaf spring (113) operable to provide frictional tension to further hold battery pack (110) within handle assembly (102). Leaf spring (113) also urges battery pack (110) into engagement with a heat sink within handle assembly (102).

Figure 4:
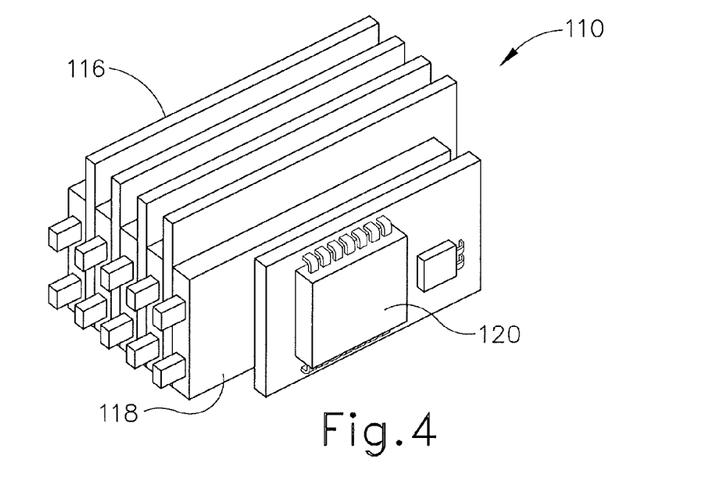
FIG. 4 depicts a perspective view of the battery pack of FIG. 3.

FIG. 4 shows battery pack (110) removed from handle assembly (102). The illustrated version depicts, for example, battery pack (110) as it is shipped or at any time prior to use. Battery pack (110) comprises a plurality of cooling plates (116) interposed between a plurality of batteries (118). Battery pack (110) further comprises a controller board (120) mounted to the outside of battery pack (110). Controller board (120) may be operable to control the discharge rate of battery pack (110). In addition or in the alternative, controller board (120) may be operable to monitor the general health of battery pack (110). Indeed, controller board (120) may be operable to provide any suitable functionality as would be apparent to one of ordinary skill in the art in view of the teachings herein.

Cooling plates (116) of the present example have a rectangular shape and are both wider and taller than batteries (118). Cooling plates (116) comprise any heat conducting material such as, but not limited to aluminum, copper, or any other suitable material as would be apparent to one of ordinary skill in the art in view of the teachings herein. While cooling plates (116) extend beyond the perimeter of batteries (118) in more than one direction in the present example, it will be appreciated that cooling plates (116) may extend in just one direction beyond the perimeter of batteries (118). While the exemplary version shows cooling plates (116) having a rectangular shape, any other suitable shape for cooling plates may be used as would be apparent to one of ordinary skill in the art in view of the teachings herein. Cooling plates (116) are operable to act as a heat sink such that when batteries (118) heat up, cooling plates (116) draw the heat away from batteries (118) and dissipate the heat by radiating heat out to atmospheric air.

Handle assembly (102) includes a plurality of vent holes (101). Vent holes (101) are operable to vent heat that has been drawn away from batteries (118). It will be understood that batteries (118) may operate in a relatively cooler state as a result of cooling plates (116) and/or vent holes (101). In some versions, cooling plates (116) are in thermal communication with separate heat sinks proximate to battery compartment (112) such that cooling plates (116) may draw heat away from batteries (118) and transfer heat to the heat sinks, which are operable to further dissipate the heat. Leaf spring (113) further aids in dissipation of heat by biasing batteries (118) into the heat sinks.

III. Exemplary Wax Cooling

Figure 5:
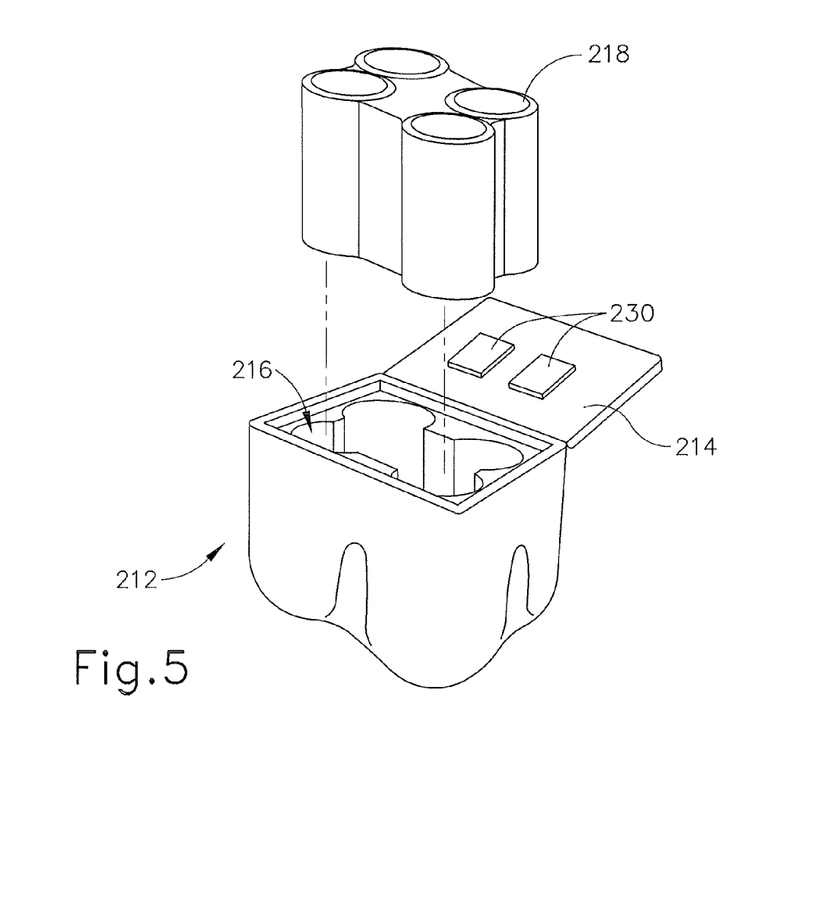
FIG. 5 depicts a perspective view of an exemplary battery compartment and battery pack.
Figure 6:
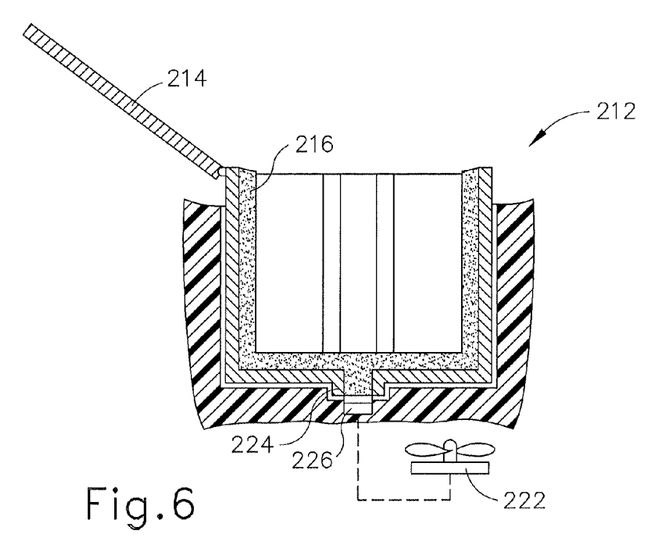
FIG. 6 depicts a side cross sectional view of the battery compartment of FIG. 5.

FIGS. 5-6 show additional exemplary features for cooling a power source such as power source (14, 111) of instrument (10, 150). In particular, FIGS. 5-6 show an exemplary battery compartment (212) having a lid (214) and a wax lining (216) operable for use with an electrically powered surgical instrument. Battery compartment (212) is operable to hold a battery pack (218). In the present example, battery pack (218) comprises a plurality of batteries bound together. In other versions, battery pack (218) may comprise any suitable number of batteries, including a single battery, for insertion into battery compartment (212). Wax lining (216) is contoured to snuggly fit around battery pack (218) once battery pack (218) is inserted into battery compartment (212). Lid (214) in the present example comprises a hinged cover, but any suitable lid may be used as would be apparent to one of ordinary skill in the art in view of the teachings herein. For example, lid (214) may comprise a sliding door, a screw on cap, or any other suitable type of lid (214). Lid (214) further comprises a set of electrical contacts (230) such that once battery pack (218) is inserted into battery compartment (212), lid (214) may be closed and contacts (230) establish electrical communication with battery pack (218). Contacts (230) extend through lid (214) such that when battery compartment (212) is inserted into surgical instrument (10) (e.g. as shown in FIG. 1), contacts (230) establish electrical communication with suitable electronic components (e.g. control module (12, 121), trigger (18), etc.) of surgical instrument (10, 150) thereby enabling battery pack (218) to deliver power to surgical instrument (10, 150).

Figure 7:
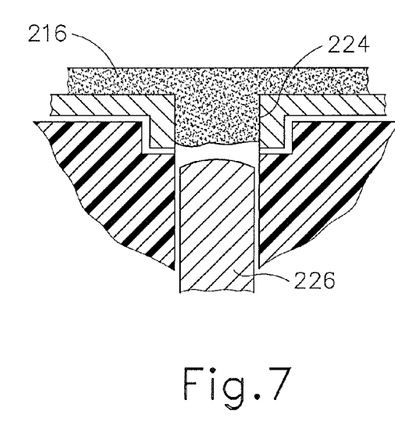
FIG. 7 depicts a side view of a wax channel of the battery compartment of FIG. 5.
Figure 8:
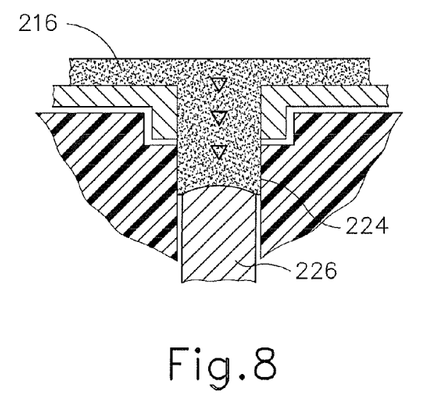
FIG. 8 depicts a side view of the wax channel of FIG. 7 with a plunger button being actuated.

As battery pack (218) delivers power to a surgical device, battery pack (218) may become heated in such a way where it may be desirable to dissipate or otherwise draw heat away from battery pack (218). As battery pack (218) heats up, wax lining (216) melts such that wax lining (216) travels downward toward a wax channel (224) positioned at the bottom of battery compartment (212) as seen in FIGS. 7-8. Wax lining (216) enters wax channel (224) and engages a plunger button (226). Plunger button (226) is in communication with a fan blower (222) as can be seen in FIG. 6. The weight of wax lining (216) against plunger button (226) is operable to push plunger button (226) downward. Plunger button (226) thereby activates fan blower (222). Fan blower (222) in the present example is pointed toward battery compartment (212) such that fan blower (222) is operable to blow air toward battery pack (218), thereby cooling battery pack (218). It will be appreciated that once battery pack (218) begins to cool, wax lining (216) may begin to contract, thus drawing wax lining (216) upwards through wax channel (224). Plunger button (226) then becomes disengaged and fan blower (222) shuts off. In some exemplary versions, it will be appreciated that battery pack (218) may be used in conjunction with one or more heat sink fins that are attached to battery compartment (212) and are operable to draw heat away from battery pack (218). It will be understood that fan blower (222) may be operable to blow air toward these heat sink fins to facilitate drawing heat away from battery pack (218). In addition or in the alternative, battery compartment (212) may be attached to angled heat sink fins enclosed in plastic, which may be operable to create air channels. As a result, when fan blower (222) blows upward, more air may be pulled away from battery compartment (212) thereby allowing better cooling of battery compartment (212).

IV. Exemplary Thermal Lining

Figure 9:
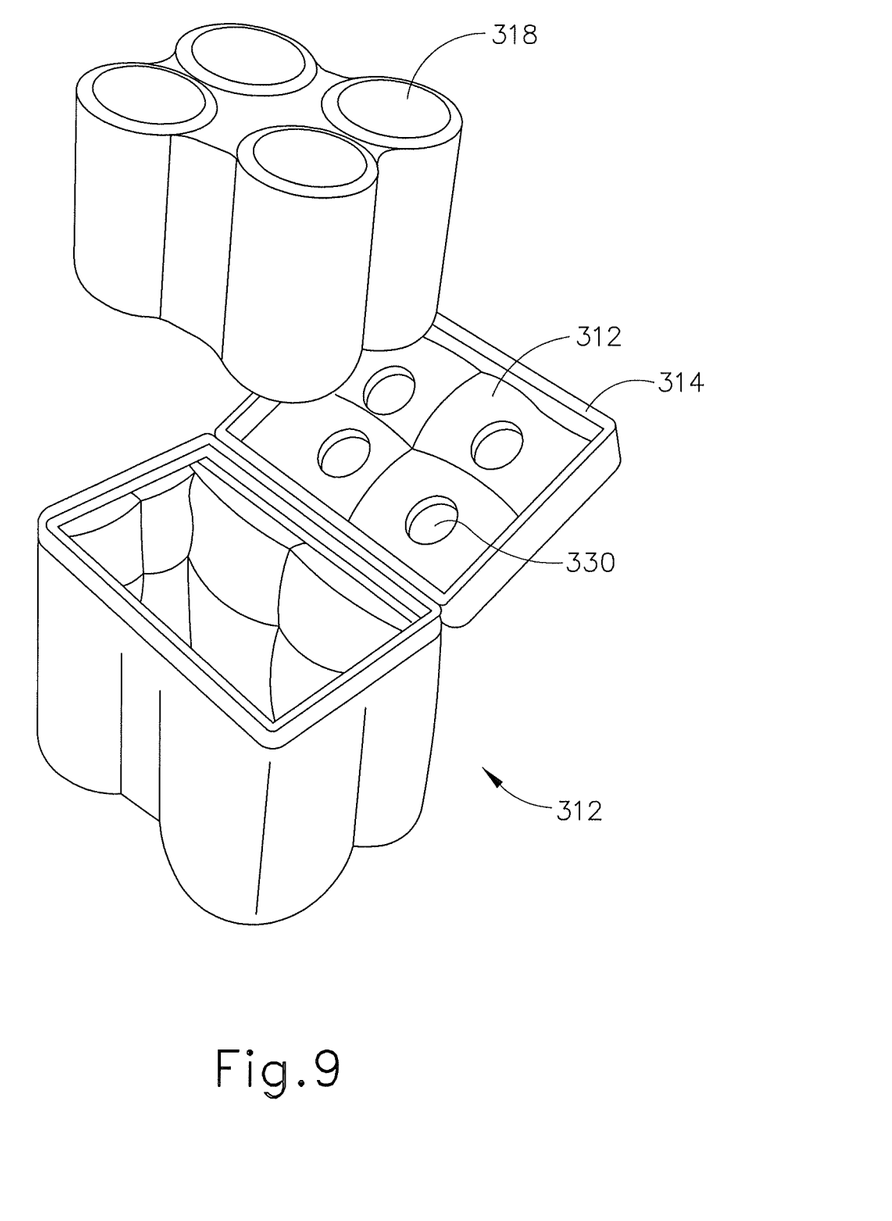
FIG. 9 depicts a perspective view of an exemplary alternative battery compartment.

FIG. 9 shows yet further exemplary features for cooling a power source such as power source (14, 111) of instrument (10, 150). In particular, FIG. 9 shows yet another exemplary battery compartment (312) that is operable to hold a battery pack (318). Battery compartment (312) comprises a lid (314) operable to close battery compartment (312). Lid (314) comprises a plurality of contacts (330) operable to engage battery pack (318) to electrically connect battery pack (318) to, for example, components of surgical instrument (10, 150). The inside of battery compartment (312) comprises a thermal lining (316) that covers all sides of the inside of battery compartment (312). In the present example, thermal lining (316) may comprise a gel and/or bladder. It will be appreciated that thermal lining (316) may be deformable such that thermal lining (316) may conform to the contours of battery pack (318). Furthermore, thermal lining (316) has a high factor of thermal conductivity such that if battery pack (318) becomes heated, then thermal lining (316) is operable to absorb heat and draw heat away from battery pack (318). It is understood that thermal lining (316) may be operable to pull heat away from battery pack (318) and transfer such heat to the external surface of battery compartment (312). In some exemplary versions, thermal lining (316) comprises an antiseptic that may be punctured and thereby aid in reclamation by allowing thermal lining (316) and surrounding areas to be sterilized by the antiseptic.

V. Exemplary Packaging

Figure 10:
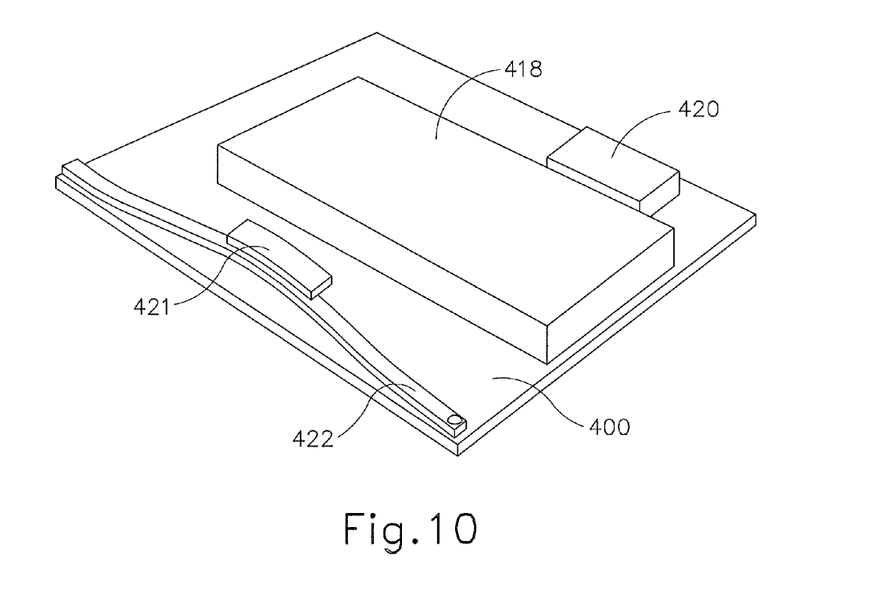
FIG. 10 depicts a perspective view of an exemplary package with a battery pack.
Figure 11:
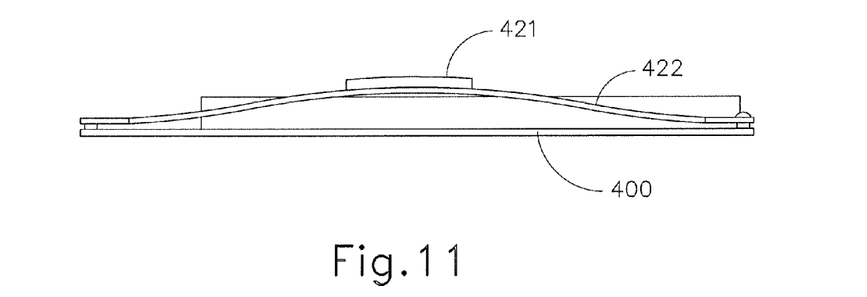
FIG. 11 depicts a side cross sectional view of the package of FIG. 10.

FIGS. 10-11 show additional exemplary features for cooling a power source such as power source (14, 111) of instrument (10, 150). In particular, FIGS. 10-11 show an exemplary platform (400) sized to accommodate a battery (418) upon platform (400). Platform (400) may be placed within surgical instrument (10, 150). Platform (400) comprises a rigid material such as a plastic, metal, or any other suitable material as would be apparent to one of ordinary skill in the art in view of the teachings herein. In addition to battery (418), platform (400) contains a cooling device (420). Cooling device (420) may be mounted to platform (400) near or in communication with battery (418). In the event that battery (418) comprises multiple batteries (418), it will be appreciated that cooling device (420) may be positioned between the multiple batteries (418). Cooling device (420) may comprise a fan, flapper, blower, or other suitable feature operable to create convection upon platform (400) such that heat coming from battery (418) may be blown away from battery (418). In the event that cooling device (420) is positioned between batteries (418), cooling device is operable to provide localized cooling for batteries (418) by creating air flow between batteries (418). In yet other exemplary versions, cooling device (420) may comprise a fan positioned underneath battery (418). Platform (400) further comprises a piezoelectric triggered strip (422) extending across platform (400). In some versions, strip (422) may have a flapper (421) operable to amplify oscillations of strip (422) thereby acting as a fan blade with strip (422) as described below. In some versions, flapper (421) of strip (422) may have a rectangular shape, but any suitable shape as would be apparent to one of ordinary skill in the art in view of the teachings herein may be used. Strip (422) is operable to receive a signal from, for example, a surgical instrument that may be in communication with platform (400). In some exemplary versions, if strip (422) receives, for example, a 100 Hz signal from surgical instrument, then strip (422) may be operable to oscillate at 100 Hz, thereby providing air flow to battery (418). In some exemplary versions, if strip (422) receives, for example, a 1,000 Hz signal from the surgical instrument, then strip (422) may be operable to oscillate at 1,000 Hz thereby creating a buzzing noise operable to indicate an error condition or other suitable message. It will be appreciated that other suitable frequency signals may be used and the discussed frequencies are merely exemplary. Strip (422) may be shaped to facilitate air flow in a particular direction such that when strip (422) oscillates, air flow travels in a single direction either toward or away from battery (418).

VI. Exemplary Potted Enclosure

Figure 12:
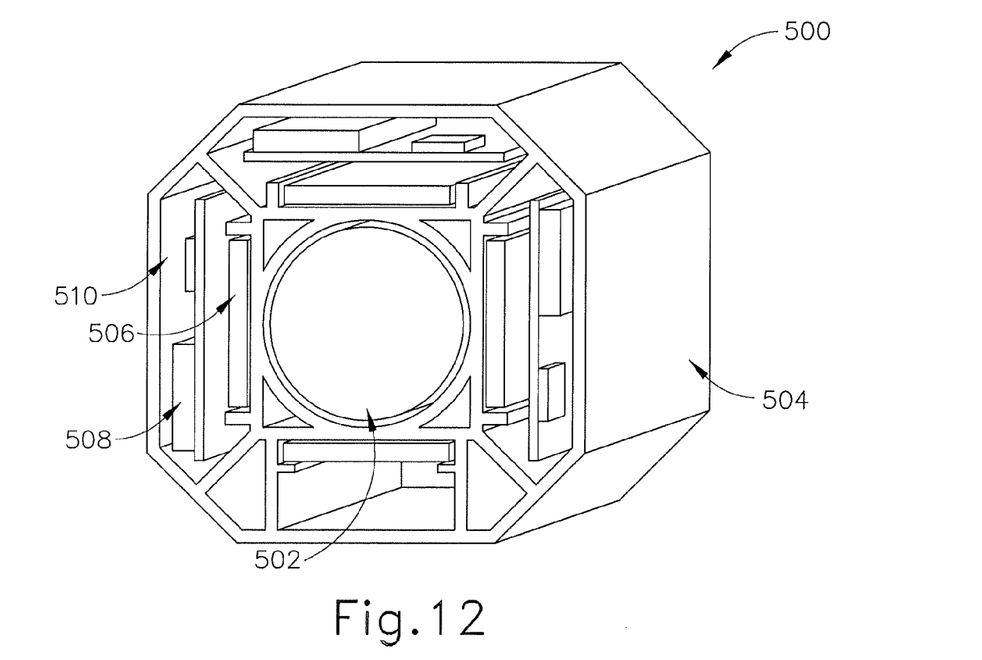
FIG. 12 depicts a perspective view of an exemplary enclosure.
Figure 13:
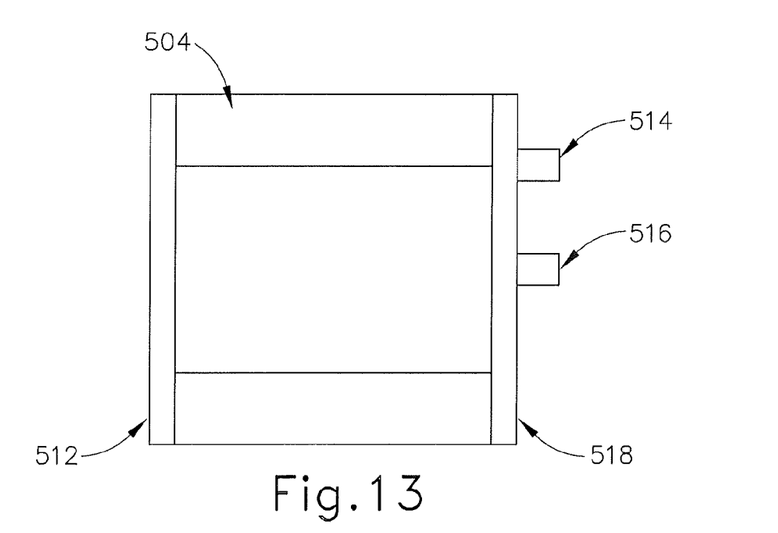
FIG. 13 depicts a side cross sectional view of the enclosure of FIG. 12.

FIGS. 12-13 show an exemplary enclosure (500) operable for use with surgical instrument (10, 150). It will be appreciated that enclosure (500) may be operable to seal components of surgical instrument (10, 150) therein and may further be operable to aid in cooling portions of surgical instrument (10, 150). Enclosure (500) comprises a motor (502), battery (506), controller module (508), and any other suitable components that would be apparent to one of ordinary skill in the art in view of the teachings herein. The aforementioned components are contained within a housing (504). In the exemplary version, housing (504) may comprise an aluminum extrusion, which may be operable to be used as a heat sink. Of course, housing (504) may be constructed of any suitable material as would be apparent to one of ordinary skill in the art in view of the teachings herein. It will be appreciated that enclosure (500) contains a substantial number of parts and/or components for operating a surgical instrument. Enclosure (500) further comprises potting (510), which is operable to hold all of the components in enclosure (500) together as well as create a fluid tight seal. It will be appreciated that potting (510) is operable to seal enclosure (500) such that steam sterilization may be used for cleaning enclosure (500). In some versions, gas plasma, ethylene oxide, and/or any other suitable method of sterilization may be used to sterilize enclosure (500) as would be apparent to one of ordinary skill in the art in view of the teachings herein. Once components are potted in enclosure (500), an endplate sealer (512) and an endcap (518) may be used to seal enclosure (500).

Once enclosure (500) is sealed, only an electrical port (514) and motor output (516) remain exposed to engage a surgical instrument, which can be seen in FIG. 13. It will be appreciated that enclosure (500) may therefore be used multiple times with sterilizations occurring between uses. In some versions, motor output (516) may comprise a rotary output shaft, a reciprocating output shaft, or any other suitable output as would be apparent to one of ordinary skill in the art in view of the teachings herein. Electrical port (514) may have a variety of suitable uses, such as, for example, recharging battery (506), providing a communication means for controlling motor (502), and/or providing an interface for monitoring the status of enclosure (500) and any parts contained therein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a surgical instrument;
   (b) a battery pack operable to power the surgical instrument, wherein the battery pack is configured to be inserted into the surgical instrument; and
   (c) a cooling device, wherein the cooling device is mechanically integrated with the battery pack, wherein the cooling device is operable to draw heat away from the battery pack while the battery pack delivers power to the surgical instrument, wherein the cooling device comprises:
   (i) a wax lining, wherein the wax lining surrounds the battery pack, wherein the wax lining is configured to melt in response to heat from the battery pack,
   (ii) a plunger button, wherein the plunger button is in fluid communication with the wax lining, wherein the plunger button is configured to be actuated by the wax lining, and
   (iii) a moving component configured to generate air flow, wherein the moving component is in communication with the plunger button, wherein the moving component is configured to selectively blow heat away from the battery pack in response to actuation of the plunger button.

2. The apparatus of claim 1, wherein the cooling device further comprises a plurality of cooling plates.

3. The apparatus of claim 2, wherein the battery pack comprises a plurality of batteries, wherein the cooling plates are alternatingly positioned between the plurality of batteries.

4. The apparatus of claim 2, wherein the cooling plates are wider and taller than the battery pack.

5. The apparatus of claim 1, wherein the cooling device further comprises a piezoelectric actuated strip, wherein the piezoelectric actuated strip comprises a first end, a second end, and a middle portion positioned between the first end and the second end, wherein the first end, the second end, and the middle portion are all aligned along a longitudinal axis, wherein the middle portion is configured to oscillate, wherein the middle portion is operable to generate airflow when a first frequency is applied to the piezoelectric actuated strip, wherein the first end and the second end are configured to maintain a stationary position as the middle portion oscillates.

6. The apparatus of claim 5, further comprising a flapper in communication with the strip, wherein the flapper is operable to amplify the airflow generated by the strip.

7. The apparatus of claim 5, wherein the strip is further operable to generate an audible signal when a second frequency is applied to the piezoelectric actuated strip.

8. The apparatus of claim 1, wherein the resilient member comprises a leaf spring, wherein the battery pack is operable to be held in the handle assembly using the leaf spring.

9. The apparatus of claim 1, wherein the cooling device further comprises a thermal lining.

10. The apparatus of claim 9, wherein the thermal lining comprises an antiseptic.

11. The apparatus of claim 1, wherein the cooling device further comprises a package operable to store the battery pack.

12. The apparatus of claim 1, wherein the battery pack and the cooling device are in thermal communication with a heat sink.

13. An apparatus comprising:
   (a) a surgical instrument;
   (b) a battery pack operable to power the surgical instrument; and
   (c) a cooling device, wherein the cooling device is operable to draw heat away from the battery pack, wherein the cooling device comprises:
   (i) a wax lining, wherein the wax lining is configured to melt in response to heat from the battery pack,
   (ii) a plunger button, wherein the plunger button is in fluid communication with the wax lining, wherein the plunger button is configured to be actuated by the wax lining, and (iii) a moving component configured to generate air flow across the battery pack, wherein the moving component is in communication with the plunger button, wherein the moving component is configured to selectively generate air flow across the battery pack in response to actuation of the plunger button.

14. An apparatus comprising:
   (a) a surgical instrument;
   (b) a battery pack in communication with the surgical instrument; and
   (c) a cooling device in communication with the battery pack, wherein the cooling device is operable to draw heat away from the battery pack while the battery pack delivers power to the surgical instrument, wherein the cooling device comprises:
   (i) a wax lining, wherein the wax lining is configured to melt in response to heat from the battery pack,
   (ii) a plunger button, wherein the plunger button is in fluid communication with the wax lining, wherein the plunger button is configured to be actuated by the wax lining, and
   (iii) a moving component configured to generate air flow, wherein the moving component is in communication with the plunger button, wherein the moving component is configured to selectively cool the battery pack in response to actuation of the plunger button.

* * * * *